(12) United States Patent
Nelwan et al.

(10) Patent No.: US 8,583,222 B2
(45) Date of Patent: Nov. 12, 2013

(54) ECG DATA DISPLAY METHOD FOR RAPID DETECTION OF MYOCARDIAL ISCHEMIA

(75) Inventors: Stefan P. Nelwan, Maasland (NL); Wolfgang Scholz, Beverly, MA (US)

(73) Assignee: Draeger Medical Systems, Inc., Telford, PA (US)

( * ) Notice: Subject to any disclaimer, the term of this patent is extended or adjusted under 35 U.S.C. 154(b) by 37 days.

(21) Appl. No.: 13/203,720

(22) PCT Filed: Feb. 26, 2010

(86) PCT No.: PCT/US2010/025509
§ 371 (c)(1), (2), (4) Date: Dec. 12, 2011

(87) PCT Pub. No.: WO2010/099386
PCT Pub. Date: Sep. 2, 2010

(65) Prior Publication Data
US 2012/0083706 A1 Apr. 5, 2012

Related U.S. Application Data

(60) Provisional application No. 61/155,775, filed on Feb. 26, 2009.

(51) Int. Cl.
*A61B 5/04* (2006.01)
*A61B 8/00* (2006.01)

(52) U.S. Cl.
USPC ............ 600/523; 600/513; 600/514; 600/517

(58) Field of Classification Search
USPC .......................... 600/450, 513–514, 517, 523
See application file for complete search history.

(56) References Cited

U.S. PATENT DOCUMENTS

| | | | |
|---|---|---|---|
| 3,811,040 A | 5/1974 | Weinfurt et al. | |
| 6,721,591 B2 | 4/2004 | Wei et al. | |
| 7,266,408 B2 | 9/2007 | Bojovic et al. | |
| 2004/0111021 A1* | 6/2004 | Olson | 600/407 |
| 2009/0275846 A1 | 11/2009 | Costa Ribalta et al. | |

FOREIGN PATENT DOCUMENTS

| WO | WO 2006033038 | 3/2006 |
|---|---|---|
| WO | WO 2008064682 | 6/2008 |
| WO | WO 2009077915 | 6/2009 |

OTHER PUBLICATIONS

ACC/AHA 2002 Guideline Update for Management of Patients with Unstable Angina and Non-ST-Segment Elevation Myocardial Infarction, J Am Coll Cardiol 2002; 40:1366-1374.

Anderson et al., "The ST Compass: spatial visualization of ST-segment deviations and estimation of the ST injury vector," ScienceDirect, Journal of Electrocardiology, received Nov. 1, 2009;www.jecgonline.com; vol. 43, Issue 2, pp. 121-131, Mar. 2010.

(Continued)

*Primary Examiner* — Nicole F Lavert
(74) *Attorney, Agent, or Firm* — Mintz Levin Cohn Ferris Glovsky and Popeo, P.C.

(57) ABSTRACT

Measured values of ST segment deviations obtained from a multi-lead ECG are transformed and displayed on a polar ST Circle Display, with zero ST deviation values located on a circle having a diameter that is greater than a maximum absolute ST segment deviation value obtained for any measured or derived lead. An ischemic condition and a location of the ischemia can thereby be easily determined.

12 Claims, 6 Drawing Sheets

(56) References Cited

OTHER PUBLICATIONS

Bacharova et al., "The Dipolar ElectroCARdioTOpographic (DECARTO) like method for graphic presentation of location and extent of area at risk estimated from ST-segment deviations in patients with acute myocardial infarction," ScienceDirect, Journal of Electrocardiology 42 (2009) 172-180.

Drew et al., "Comparison of a New Reduced Lead Set ECG With the Standard ECG for Diagnosing Cardiac Arrhythmias and Myocardial Ischemia," Journal of Electrocardiology vol. 35 Supplement 2002.

Horacek, et al., "On designing and testing transformations for derivation of standard 12-lead/18-lead electrocardiograms and vectorcardiograms from reduced sets of predictor leads," ScienceDirect, Journal of Electrocardiology 41 (2008) 220-229.

Pahlm-Webb, et al., "A New Method for Using the Direction of ST-Segment Deviation to Localize the Site of Acute Coronary Occlusion: The 24-View Standard Electrocardiogram," Am J Med. 2002;113:75-78.

Van Herpen, et al., "Are Additional Right Precordial and Left Posterior ECG Leads Useful for the Diagnosis of Right Ventricular Infarct and Posterior Infarct?," Journal of Electrocardiology vol. 32 Supplement 1999.

\* cited by examiner

ECG DATA DISPLAY METHOD FOR RAPID DETECTION OF MYOCARDIAL ISCHEMIA

CROSS-REFERENCE TO RELATED APPLICATIONS

This application is filed under 35 U.S.C. 371 as a U.S. national phase application of PCT/US2010/025509, having an international filing date of 26 Feb. 2010, which claims the benefit of U.S. Provisional Patent Application No. 61/155,775, having a filing date of 26 Feb. 2009, both of which are hereby incorporated by reference.

BACKGROUND OF THE INVENTION

Routine electrocardiogram (ECG) monitoring is standard practice in coronary and intensive care units, emergency rooms, ambulatory monitoring settings and operating rooms. Frequently, continuous ST segment monitoring is carried out in order to detect ST changes which may indicate ischemic episodes. Data obtained from such a monitoring are automatically displayed on a monitor to show a clinician the status of the patient. For carrying out an ECG test, a variable number of ECG electrodes are positioned on a patient in a way that the electrodes form a predefined arrangement, e.g. accordingly to "Einthoven", "Goldberger" and "Wilson", EASI, "Frank" or others. A standard 12-lead ECG may have, for example, six vertical leads of a 12-lead-ECG, namely aVF, III, aVL, I, aVR and II (clockwise). Thereby the bipolar "Einthoven" leads I, II and III and the unipolar "Goldberger" leads aVR, aVL and aVF are used. The displayed values can be obtained from a mathematical linear combination of the values of the electrical voltages obtained from the ECG electrodes. The position of the axes in the displayed image and their angles represent the location of its corresponding ECG electrodes on the patient's body during the ECG test.

Likewise, six axes relating to the six horizontal "Wilson" leads of a 12-lead-ECG, namely $V_1, V_2, \ldots V_6$ are used. Again the position of these axes and their angles represent the location of its corresponding ECG electrode on the patient's body during the ECG test. Not all the leads need to be measured, as some of the leads can be derived from a linear combination of other leads.

One of the clinically important uses of the ECG is to detect acute myocardial infarction and indicate the location and even the extent of the jeopardized myocardium, because acute transmural ischemia caused by occlusion of a major coronary artery produces an epicardial injury current that can be detected as a deviation of the ST segment toward the involved region. Depending on the degree of the ischemic event, the ECG will show an ST depression (negative voltage) or an ST elevation (positive voltage). For the left anterior descending coronary artery, this typically appears as ST elevation maximal in precordial leads $V_2$ or $V_3$, and for the right coronary artery, as ST elevation maximal in limb leads aVF or III. However, except when the left circumflex coronary artery is dominant (supplies the posterior descending artery), its acute occlusion is represented instead by ST depression maximal in leads $V_2$ or $V_3$. The elevation or depression of the ST segment in a particular lead combination will point to the particular area of the heart that experiences an ischemic event.

The method of ECG display can enhance or obscure the diagnostic information needed to support the therapeutic decisions made for patients with acute coronary syndromes. The classic display includes two segregated groups of the six limb leads (I, II, and III; and aVR, aVL, and aVF) and two integrated groups of the six precordial leads. The limb leads are typically regrouped into a single orderly sequence, which includes locating inverted aVR (−aVR) between leads I and II to create an integrated logical display of cardiac electrical activity in the frontal plane, similar to that used in the classic display for the precordial leads. With these displays, the zero voltage ST-segment deviation is then located at the center of the display, which makes allocation of the direction of ST-segment deviation to localize the site of acute coronary syndrome difficult.

Accordingly, there is a need for an improved display format for the limb leads and the precordial leads which improves the clinical value of a standard ECG, for example, for the detection of myocardial infarction and the evaluation of intra- and post-operative ischemia.

BRIEF SUMMARY OF THE INVENTION

According to one aspect of the invention, a method for displaying multi-lead ECG data with a patient monitoring device includes the steps of determining from a plurality of ECG leads corresponding ST-segment deviations, determining a maximum value of the ST-segment deviations, defining in a polar diagram a zero ST-segment deviation by a concentric circle having a radius having a value of greater than a maximum magnitude of all determined ST-segment deviations, modifying determined ST-segment deviations by the adding the value of the radius to all determined ST-segment deviations, and displaying the modified ST-segment deviations on the patient monitoring device in the polar diagram according to axial directions defined by the ECG leads.

According to another aspect of the invention, a patient monitoring device for display of ST segment deviations in an ECG includes an input receiving signals from ECG leads, and a processor configured to determine from the signals ST segment deviations and, if required, computing ST segment deviation values of non-measured ECG leads. The processor is further configured to determine a maximum value of the ST-segment deviations, define in a polar diagram a zero ST-segment deviation by a concentric circle having a radius having a value of greater than a maximum magnitude of all determined ST-segment deviations, and modify the determined ST-segment deviations by the adding the value of the radius to all determined ST-segment deviations. The patient monitoring device further includes a display for displaying the modified ST-segment deviations on the patient monitoring device in the polar diagram according to axial directions defined by the ECG leads.

Embodiments of the invention may include one or more of the following features. ST-segment deviations for missing ECG leads may be computed from a linear combination of ST-segment deviation values of measured ECG leads. The conventional order of the ECG leads in the polar diagram of the ST Circle Display is maintained. Myocardial ischemia is defined by an ST-segment deviation in two contiguous leads of at least 0.1 mV. Accordingly, deviations of the modified ST-segment deviations from a circle, in particular a circle having its center at the origin, are assessed and the presence of myocardial ischemia is ascertained from the observed deviation.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

Figure 1:
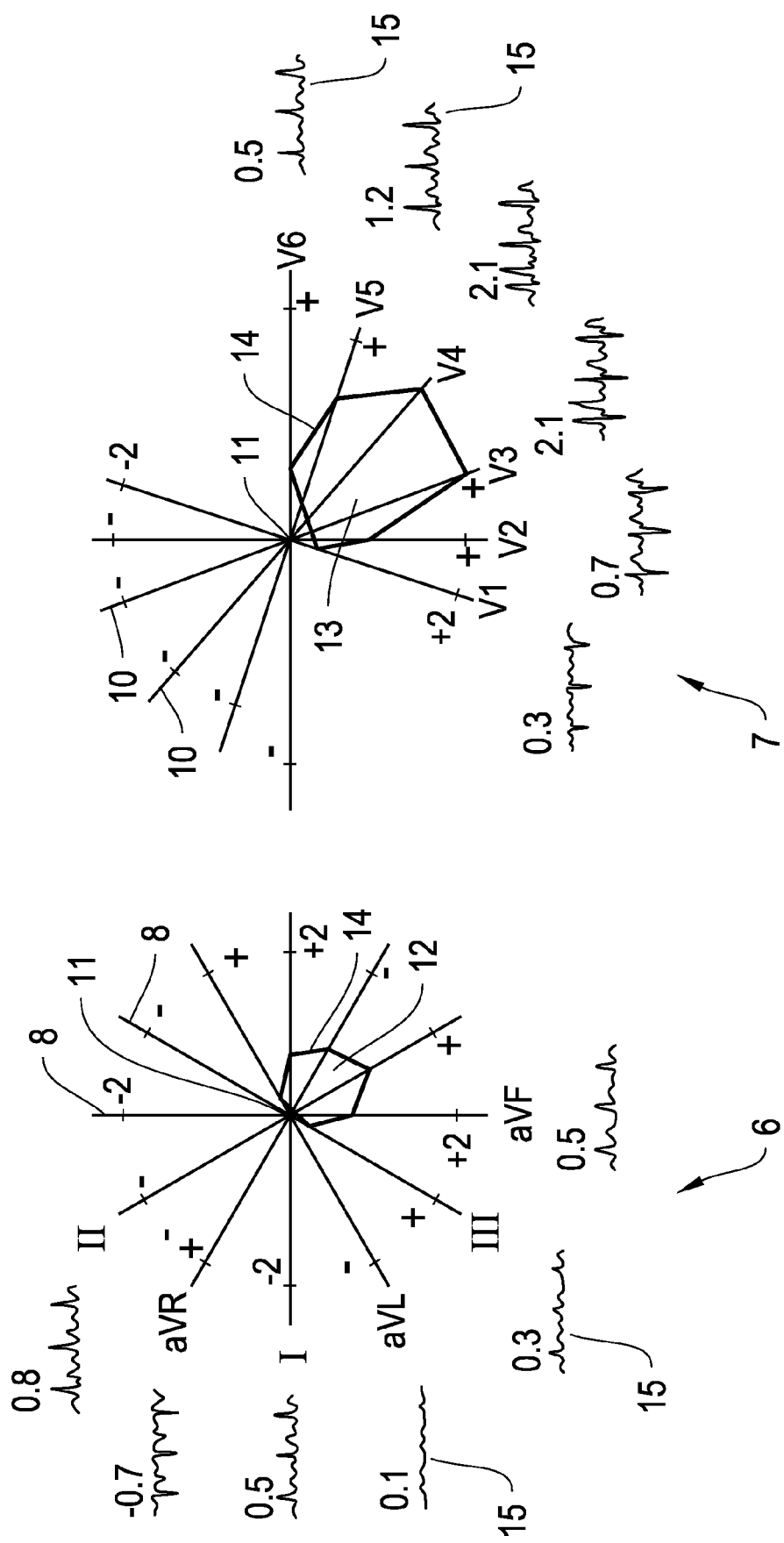
FIG. 1 is a prior art frontal plane view map of ST-segment deviation.

FIG. 1 depicts two multi-axis diagrams 6, 7 as they are displayed on a monitor. The diagrams 6, 7 are used to represent the ST lead values of a common 12-Lead ECG as a three-dimensional view.

The diagram 6 on the left hand side represents the vertical plane of the two-dimensional subspace in which the cardiac electrical field of the heart is projected. Therefore this diagram 6 consists of six axes 8 representing the six vertical ST leads of a 12-lead-ECG, namely aVF, III, aVL, I, aVR and II (clockwise). Thereby the bipolar "Einthoven" leads I, II and III and the unipolar "Goldberger" leads aVR, aVL and aVF are used. The displayed values are obtained from the mathematical linear combination of the values of the electrical voltages obtained from the actual ECG electrodes. The position of the axes 8 and its angle represent the location of its corresponding ECG electrode 2 on the patient's body during the ECG test. Thereby the following scheme is applied:

| Axis | Angle |
|---|---|
| I | 0° |
| II | 60° |
| III | 120° |
| aVR | −150° |
| aVL | −30° |
| aVF | 90° |

The diagram 7 on the right hand side represents the horizontal plane and therefore consists of six axes 10 relating to the six horizontal "Wilson" ST leads of a 12-lead-ECG, namely $V_6, V_5, \ldots, V_1$ (clockwise) are used. Again the position of these axes 10 and its angle represent the location of its corresponding ECG electrode 2 on the patient's body during the ECG test. Thereby the following scheme is applied:

| Axis | Angle |
|---|---|
| $V_1$ | 120° |
| $V_2$ | 90° |
| $V_3$ | 75° |
| $V_4$ | 60° |
| $V_5$ | 30° |
| $V_6$ | 0° |

Each axis 8, 10 of the diagrams 6, 7 is assigned to one parameter. In both diagrams 6, 7 all the axes 8, 10 run from negative values to positive values (or vice versa) through a zero-point 11, which represents a zero voltage signal in a lead. The directions of the axes 8, 10 are shown using "+" and "−" signs nearby the axes. For example the aVF axis leading downwards from the center of the diagram 6 represent positive values, whereas the aVL axis leading in the lower left corner of the diagram 6 represent negative values.

The values displayed on the six axes 8, 10 in each diagram 6, 7 are connected in order to form a polygonal pattern 12, 13 accentuated by a thick line 14, which may be used for easy recognition of the patient's situation. The shape of the pattern 12, 13 gives information not only about the current values of the ST leads but also about the spatial arrangement of the ECG data. For example, the right hand side diagram 7 in FIG. 1, which illustrates the horizontal plane, suggests a possible ischemic disease located within the fore side of the heart. The diagram 6 on the left hand side, which illustrates the vertical plane, suggests a possible disease located in a lower region of the heart. Both diagrams 6, 7 can be combined to provide full three-dimensional information that the disease may most likely be located in a lower region of the fore side of the patient's heart.

Additional information in form of a PQRST complex 15 (so called ST snippet) of the corresponding lead is displayed at the end of the axes 8, 10. This seeks to clarify and extend the comprehension of the information they provide. Above each ST snippet 15 the value of the ST elevation or depression is displayed.

One of the principal techniques employed to interpret ECG data is the analysis of ST segment deviations and T-wave abnormalities. For example, ST deviations may be used to predict the likelihood that a patient's symptoms are due to myocardial ischemia. This is particularly true if the changes are new or transient. ST segment and T-wave changes also contribute significantly to risk assessment. Patients with extensive changes in their ST segment (e.g., elevation or depression) are generally at higher short-term risk of death than patients with no or minimal changes (ACC/AHA 2002 Guideline Update for Management of Patients with Unstable Angina and Non-ST-Segment Elevation Myocardial Infarction, J Am Coll Cardiol 2002; 40:366-74).

Although information regarding ST segments is of critical importance in assessing patients with myocardial ischemia, standard 12-lead ECG techniques may underemphasize or completely fail to detect such events. A ST-segment depression or elevation of greater than 0.1 mV may correlate to a positive inference of ischemia. This criterion (0.1 mV) may be derived from empirical data determined by interpreting standard ECG data, and has been recognized as a suitable criterion indicating ischemia. It should be obvious, however, that other ST-segment depression or elevation criteria may be used, including other empirically relevant criteria (e.g., 0.05, 0.1, 0.15 mV, 0.2 mV, etc.).

While the ST map of FIG. 1 displays the values of the ST-segment depression/elevation for the traditional 12-lead ECG, an interpretation of the generated ST maps and location of areas in the heart suffering from ischemia is not very intuitive, especially when the clinician has to diagnose and respond quickly to changing patient conditions. It has been observed by the inventors that the clinician's response to changes in the ECG is much improved by representing and displaying ECG data from patients in a form having an inherent and easily discernable symmetry, with a change in the symmetry indicative of a progression or recovery from ischemia.

Figure 3:
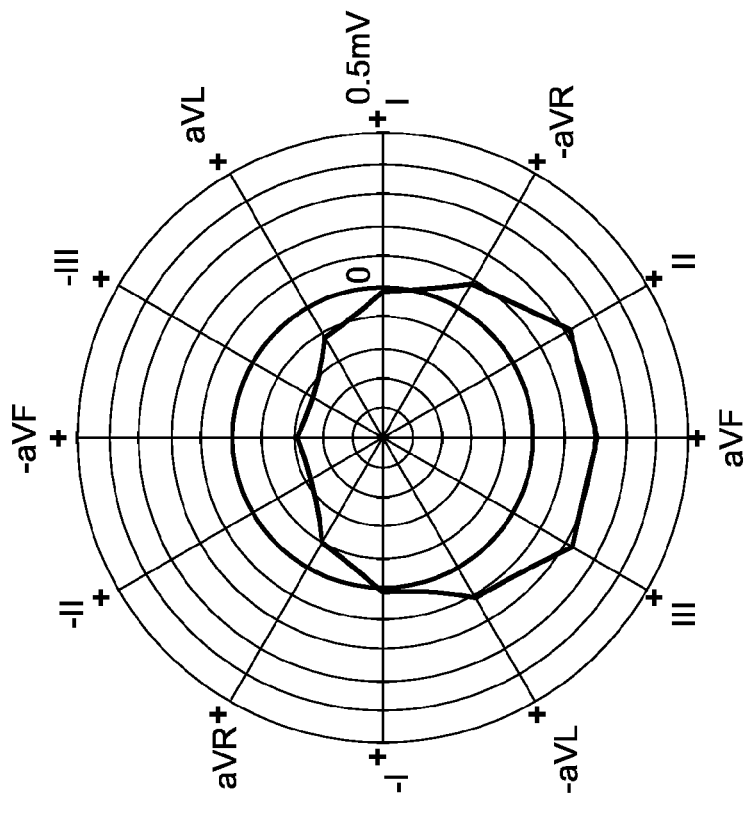
FIG. 3 is a ST Circle Display of the ST-segment deviation of FIG. 2 according to the invention.
Figure 2:
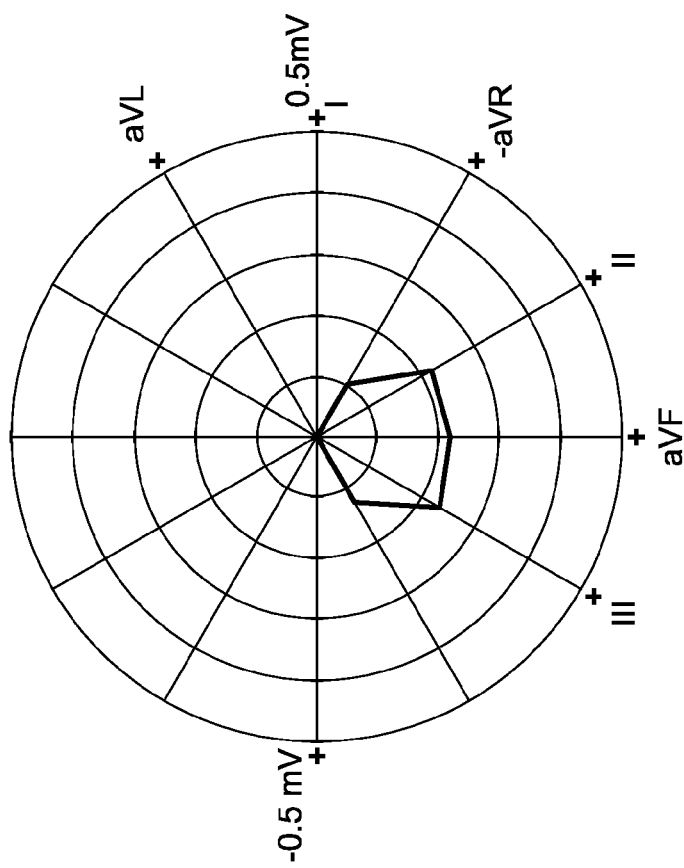
FIG. 2 is a another prior art frontal plane view map of ST-segment deviation.

FIG. 2 shows a conventional ST map of a frontal plane view with the zero value of the ST-segment deviation at the center. FIG. 3 displays the same ST-segment deviation in an ST circle display according to the invention. The axes are labeled identically in both Figures. The locus of the zero value of the ST-segment deviation in FIG. 3 is a radius selected to be greater than (for example, twice) a maximum expected ST-segment deviation. This circle is labeled "0" in FIGS. 2 to 6. For example, the measured ST-segment deviation in FIG. 3 is about 0.2 mV, so that a radius of 0.5 mV would be sufficient. As mentioned above, ST-segment deviations are rarely greater than 0.2 mV.

With the representation of FIG. 3 and taking into account the polarity of the axes, negative values of the ST-segment deviation are then located inside the circle, whereas positive values of the ST-segment deviation are located outside the circle. As is common, the display may include measured leads (e.g., I and II, possibly III) as well as computed leads (aVF, aVL, aVR). In normal subjects, the diagram in FIG. 3 is a concentric circle close to the "0" circle, while abnormal values show a shifted and/or deformed shape.

The benefit of the proposed ST-segment deviation map according to the invention becomes even clearer when displaying the transverse plane view with all the accepted derived leads ($V_7$, $V_8$, $V_9$, V3R, V4R, VSR, V6R). These leads can be directly measured and or can be derived from the conventional 12 lead ECG.

Figure 4:
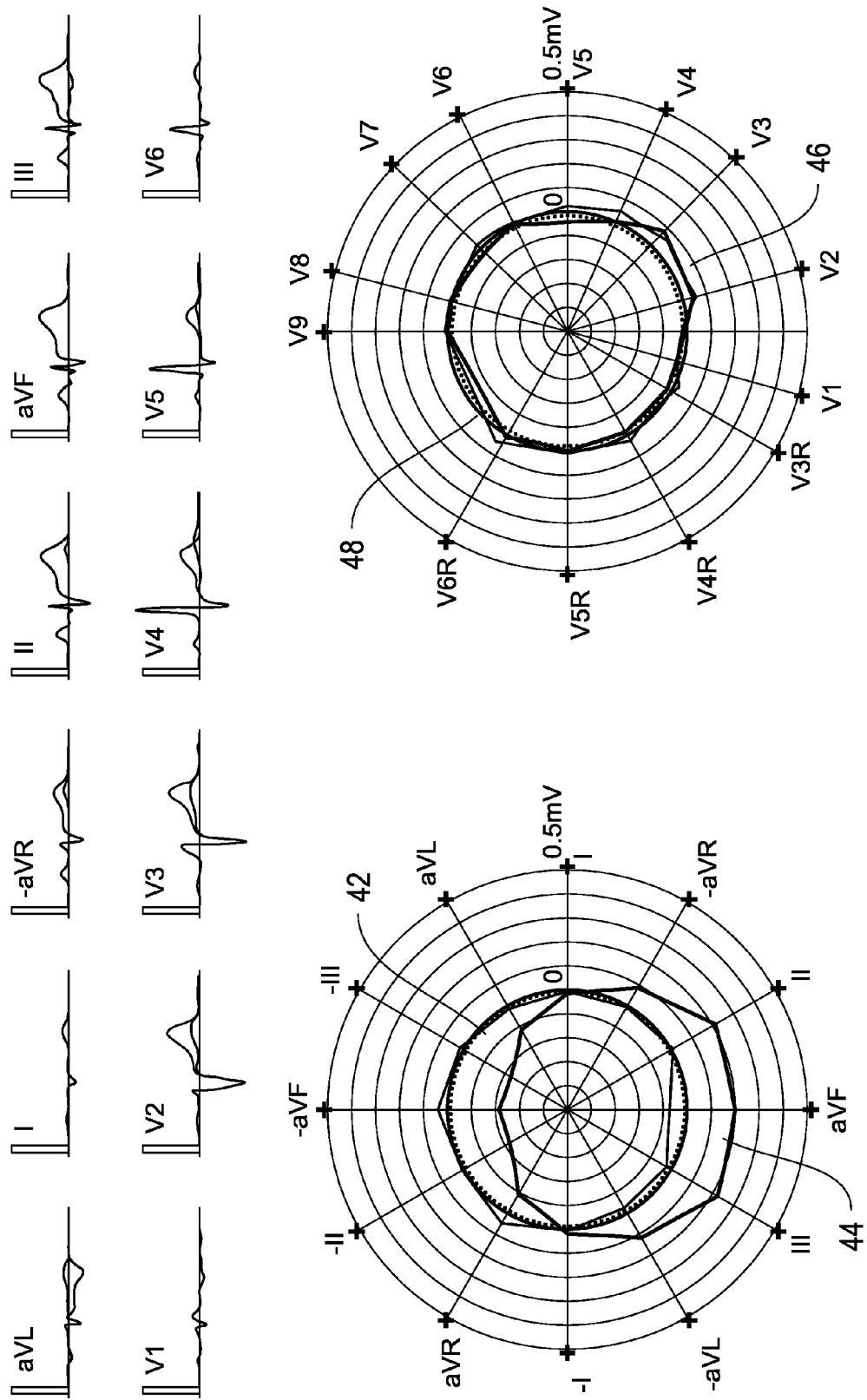
FIG. 4 shows ST-segment deviations measured in a 12-lead ECG and a frontal plane view ST Circle Display (left side) and a transverse plane view ST Circle Display (right side) of the measured ST-segment deviation according to the invention.

FIG. 4 shows an application of the invention with an actual clinical case. In this example, a patient underwent a percutaneous coronary intervention with the purpose of opening an occluded coronary artery with a balloon catheter. The traditional 12-lead ECG is shown on two rows of six leads (frontal and precordial) above the two circles. One ECG-complex reflects the situation before the intervention and the other ECG complex shows the ECG at the moment when the balloon is inflated and when the artery is fully occluded.

As a general rule, the ST-segments in all leads should be 0. Physiologically, the voltage-difference in the myocardial cells of the heart should be close to 0, because the ventricles were just activated and had contracted (in the QRS).

The plot can be used to distinguish between supply and demand ischemia. The presented clinical case is an example of supply ischemia, because the blood vessels were intentionally occluded. This type of ischemia is typically associated with ST elevations. However, demand ischemia happens when the heart requires more oxygen. This type can be seen when a patient is on a treadmill or bicycle. In this situation, ischemia is often associated with ST depression (in addition to T-wave changes).

Studies of human interaction with computers have shown that human visual perception is very sensitive to noticing small deformations from a regular shape, such as a circle. An experienced clinician will readily notice small changes in any quadrant of the circle, before the patient's condition goes from normal to ischemic. The ST Circle Display plots are shown in the lower part of FIG. 4 below the standard 12 leads. The ST Circle Display showing the ST measurements of a reference ECG (before intervention) is indicated with the reference symbol 42, and the ECG at the time of balloon inflation (where the blood vessels are intentionally occluded) with the reference symbol 44. The lines 46 in the right ST Circle Display show the ST measurements for the standard 6 precordial leads, whereas the lines 46 show the ST measurements of the derived leads (V4R-V6R, V7-V9) which are not directly measured.

Figure 5:
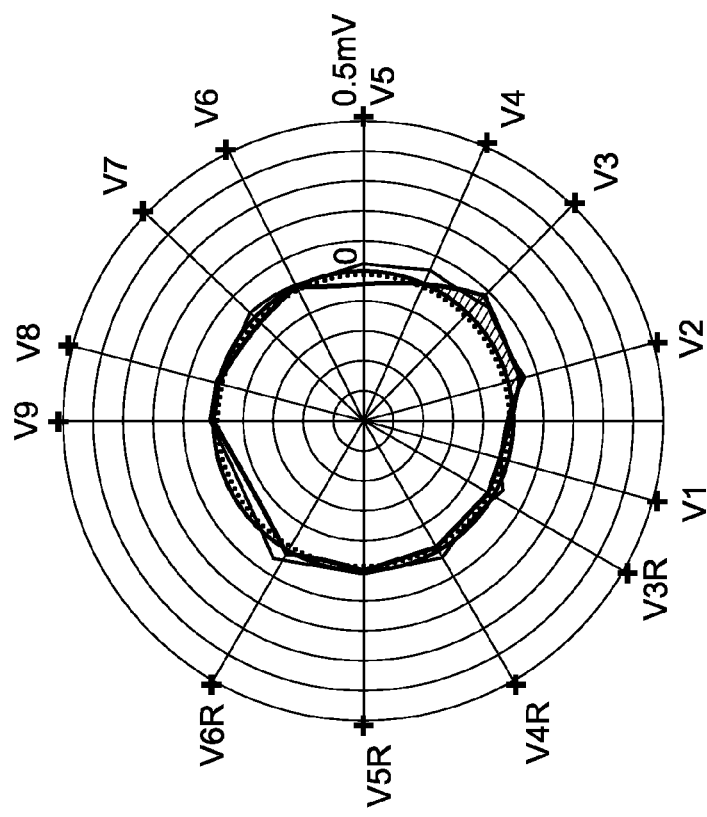
FIG. 5 shows highlighted areas in the ST Circle Display of FIG. 4 for improved representation of changes in ST-segment deviation for the same patient at two different times.
Figure 5:
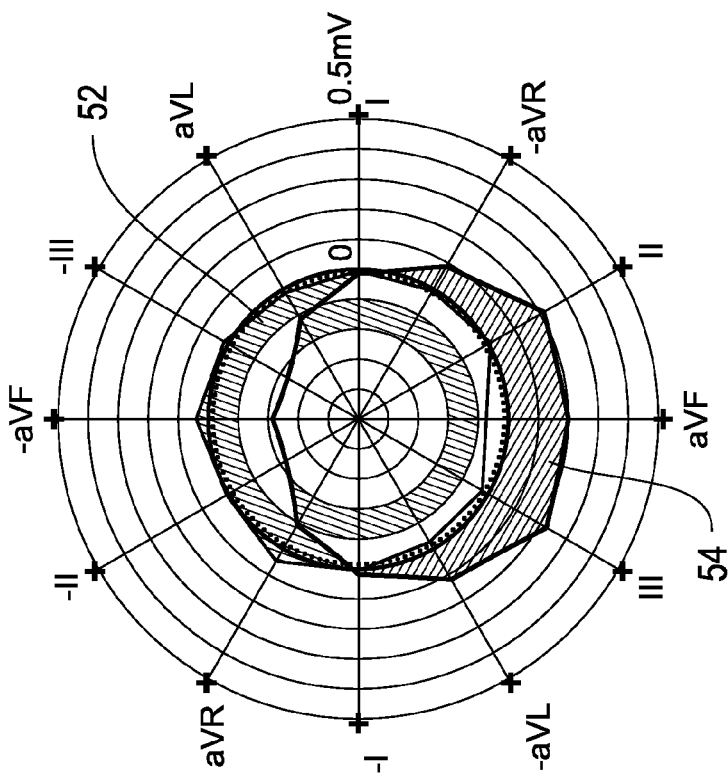

As shows in more detail in FIG. 5, the shift in the ST measurements before, during and after interventional treatment can be emphasized by highlighting areas of change 52, 54 between ST measurements. An experienced clinician will then readily notice the changes in the patient's condition.

Figure 6:
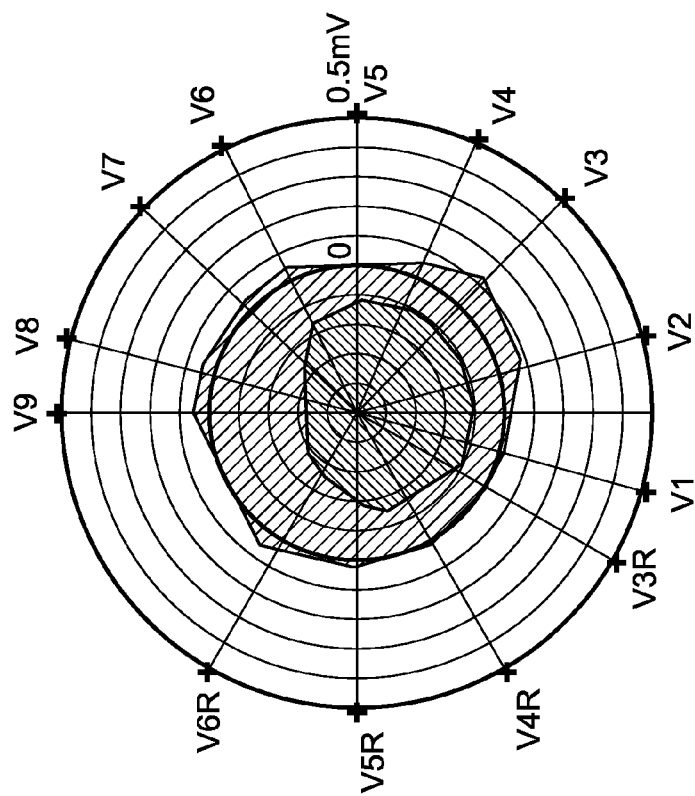
FIG. 6 shows highlighted areas in an ST Circle Display for a different patient.
Figure 6:
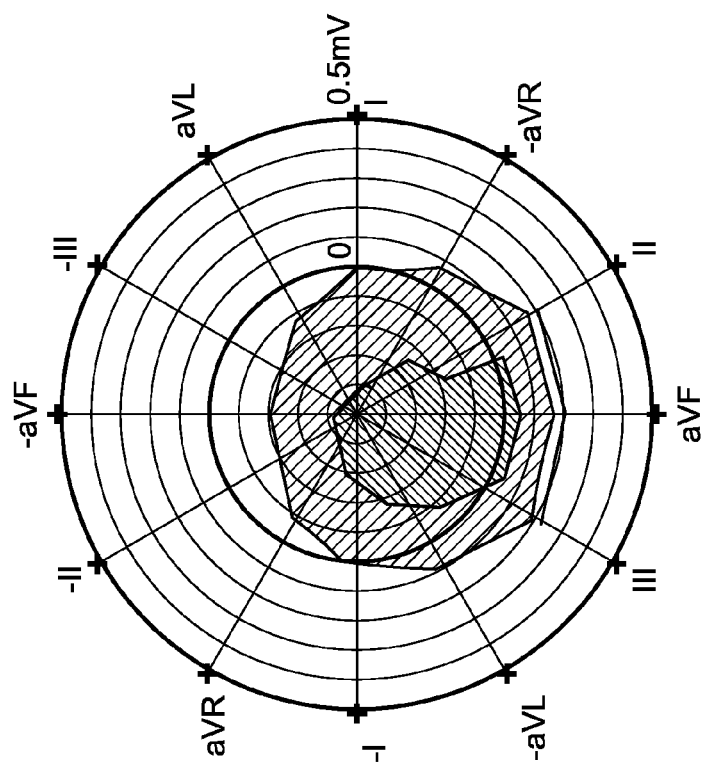

FIG. 6 shows an ST Circle Display for another patient a frontal plane view (left side) and a transverse plane view (right side) of two superimposed ST-segment deviations acquired at different times. The dark area inside the circle represents the ST-segment deviations for the patient at the time of being admitted and before a catheterization procedure. As can be readily seen, the patient suffers from acute ischemia. The overlaid gray area represents updated (current) ST-segment deviation value, indicated an improvement in the physical condition of the patient. As mentioned above, a shape of the ST-segment deviation closer to a circle indicates a normal condition (no ischemia). With the ST Circle Display of the present invention, the clinician will watch the time-evolution of the area in the ST Circle Display representing an updated current value (in gray) of the ST-segment deviation and compare the shape and position of that area with the "reference" area (black) obtained when the patient was admitted and/or before the surgical procedure.

Figure 7:
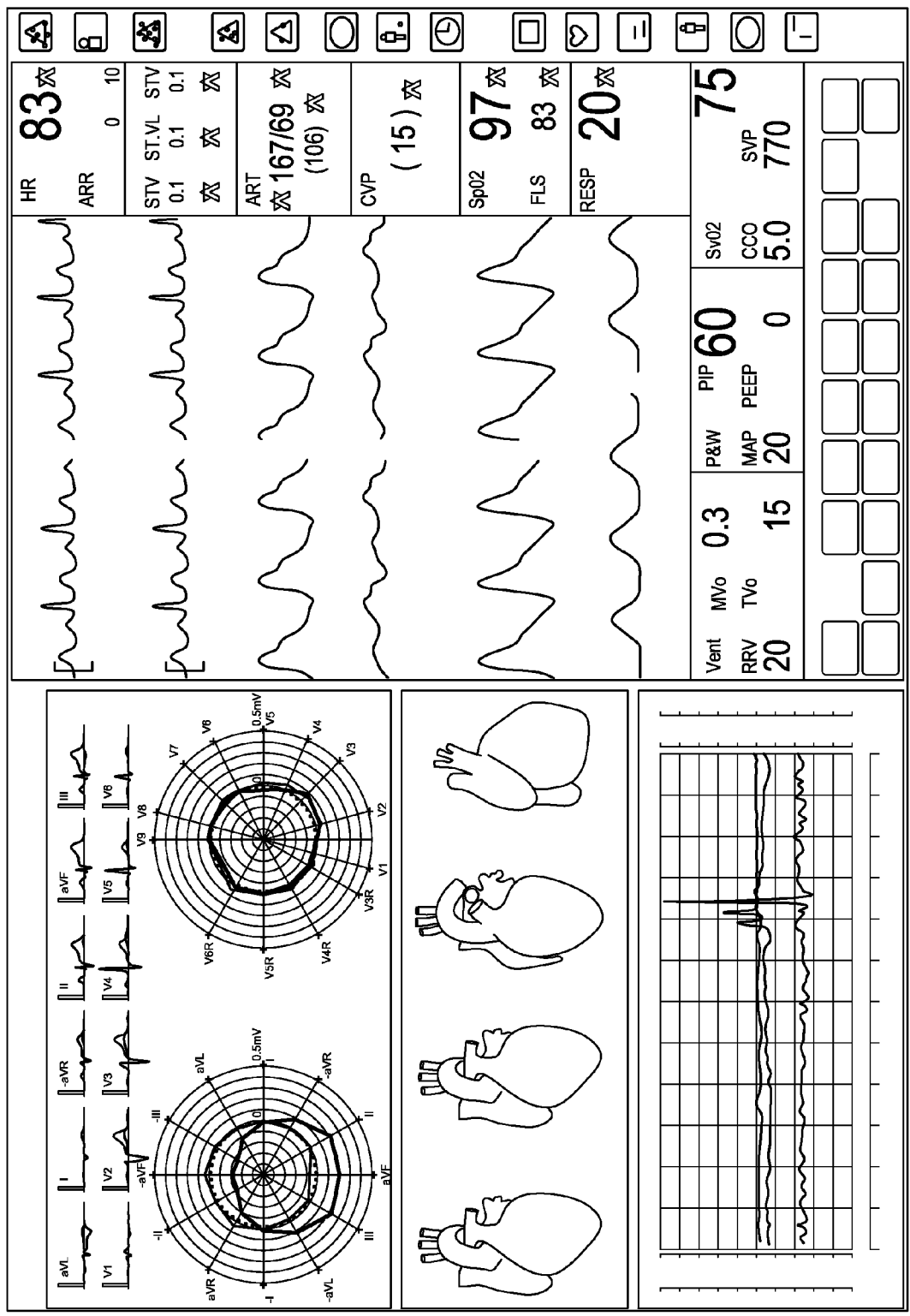
FIG. 7 is a patient monitoring device displaying the ST values and other vital signs of a patient.

FIG. 7 shows a patient monitoring device displaying the ST values and other vital signs of a patient. It will be understood that the patient monitoring device can be connected to a number of vital sign monitoring sensors, such as multi-lead ECG, SpO2, etc. The patient monitoring device includes hardware, such as a microprocessor, configured to measure the ST segment deviations and transform the measured values to ST Circle display values and/or overlay them with a model of the heart, and a display for receiving and displaying the ST Circle display values.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the invention.

What is claimed is:

1. In a patient monitoring device, a method for displaying multi-lead electrocardiogram (ECG) data, comprising:
   determining, from a plurality of ECG leads provided by an ECG device, corresponding ST-segment deviations using a microprocessor;
   determining a maximum value of the ST-segment deviations using the microprocessor;
   defining in a polar diagram a zero ST-segment deviation by a concentric circle having a radius having a value of greater than a maximum magnitude of all determined ST-segment deviations;
   transforming select determined ST-segment deviations by adding the value of the radius to all selected determined ST-segment deviations; and
   displaying the concentric circle and the transformed ST-segment deviations on the patient monitoring device in the polar diagram, the transformed ST-segment deviations displayed according to axial directions defined by the ECG leads.

2. The method of claim 1, wherein the ECG leads are displayed in the axial directions in the polar diagram with a predetermined sequential order.

3. The method of claim 1, wherein myocardial ischemia is defined by an ST-segment deviation in two contiguous leads of at least 0.1 mV, the method further comprising:
assessing deviations of the modified ST-segment deviations from a circle, in particular a circle having its center at the origin, and ascertaining the presence of myocardial ischemia from the observed deviation.

4. The method of claim 1, further comprising: computing ST-segment deviations for missing ECG leads from a linear combination of ST-segment deviation values of measured ECG leads.

5. A patient monitoring device for display of ST segment deviations in an electrocardiogram (ECG), the device comprising:
an input unit configured to receive signals from ECG leads;
a processor configured to determine from the signals ST segment deviations and, if required, computing ST segment deviation values of non-measured ECG leads,
determine a maximum value of the ST-segment deviations, define in a polar diagram a zero ST-segment deviation by a concentric circle having a radius having a value of greater than a maximum magnitude of all determined ST-segment deviations, and
transform select determined ST-segment deviations by the adding the value of the radius to all select determined ST-segment deviations; and
a display for displaying the concentric circle and the modified ST-segment deviations on the patient monitoring device in the polar diagram, the transformed ST-segment deviations displayed according to axial directions defined by the ECG leads.

6. The device of claim 5, wherein the ECG leads are displayed in the axial directions in the polar diagram with a predetermined sequential order.

7. The device of claim 5, wherein myocardial ischemia is defined by an ST-segment deviation in two contiguous leads of at least 0.1 mV, the processor further configured to assess deviations of the modified ST-segment deviations from a circle, in particular a circle having its center at the origin, and ascertain the presence of myocardial ischemia from the observed deviation.

8. The device of claim 5, wherein the processor is further configured to compute ST-segment deviations for missing ECG leads from a linear combination of ST-segment deviation values of measured ECG leads.

9. A non-transitory computer program product storing instructions, which when executed by at least one data processor, result in operations comprising:
determining, from a plurality of electrocardiogram (ECG) leads provided by an ECG device, corresponding ST-segment deviations;
determining a maximum value of the ST-segment deviations;
defining in a polar diagram a zero ST-segment deviation by a concentric circle having a radius having a value of greater than a maximum magnitude of all determined ST-segment deviations;
transforming select determined ST-segment deviations by adding the value of the radius to all selected determined ST-segment deviations; and
displaying the concentric circle and the transformed ST-segment deviations on a display device in the polar diagram, the transformed ST-segment deviations displayed according to axial directions defined by the ECG leads.

10. The non-transitory computer program product of claim 9, wherein the ECG leads are displayed in the axial directions in the polar diagram with a predetermined sequential order.

11. The non-transitory computer program product of claim 9, wherein myocardial ischemia is defined by an ST-segment deviation in two contiguous leads of at least 0.1 mV, the operations further comprising:
assessing deviations of the modified ST-segment deviations from a circle, in particular a circle having its center at the origin, and ascertaining the presence of myocardial ischemia from the observed deviation.

12. The non-transitory computer program product of claim 9, the operations further comprising: computing ST-segment deviations for missing ECG leads from a linear combination of ST-segment deviation values of measured ECG leads.

* * * * *